United States Patent [19]

Sesin et al.

[11] Patent Number: 4,868,208
[45] Date of Patent: Sep. 19, 1989

[54] ANTIFUNGAL AGENT AND METHOD

[75] Inventors: David F. Sesin, Westfield; Jerrold M. Liesch, Princeton Junction, both of N.J.

[73] Assignee: Merck & Co., Inc., Rahway, N.J.

[21] Appl. No.: 219,943

[22] Filed: Jul. 15, 1988

[51] Int. Cl.$^4$ .................................... C07D 303/02
[52] U.S. Cl. .......................... 514/475; 549/513; 549/553
[58] Field of Search .................. 549/553; 514/475

[56] References Cited

PUBLICATIONS

Kupchan et al., J. Am. Chem. Soc., 94, 1354 (1972).

Primary Examiner—Glennon H. Hollrah
Assistant Examiner—Amelia A. Owens
Attorney, Agent, or Firm—Alice O. Robertson; Joseph F. DiPrima

[57] ABSTRACT

Novel semi-synthetic antifungal compounds which may be produced from 10-[(3-chloro-4-methoxyphenyl)methyl]-6- methyl-3-(2-methylpropyl)-16-[1-(3-phenyloxiranyl)ethyl]-1,4-dioxa- 8,11-diazacyclohexadec-13-ene-2,5,9,12-tetrone isolated from the fermentation of a cyanobacterium (Nostoc sp.) are described.

5 Claims, 1 Drawing Sheet

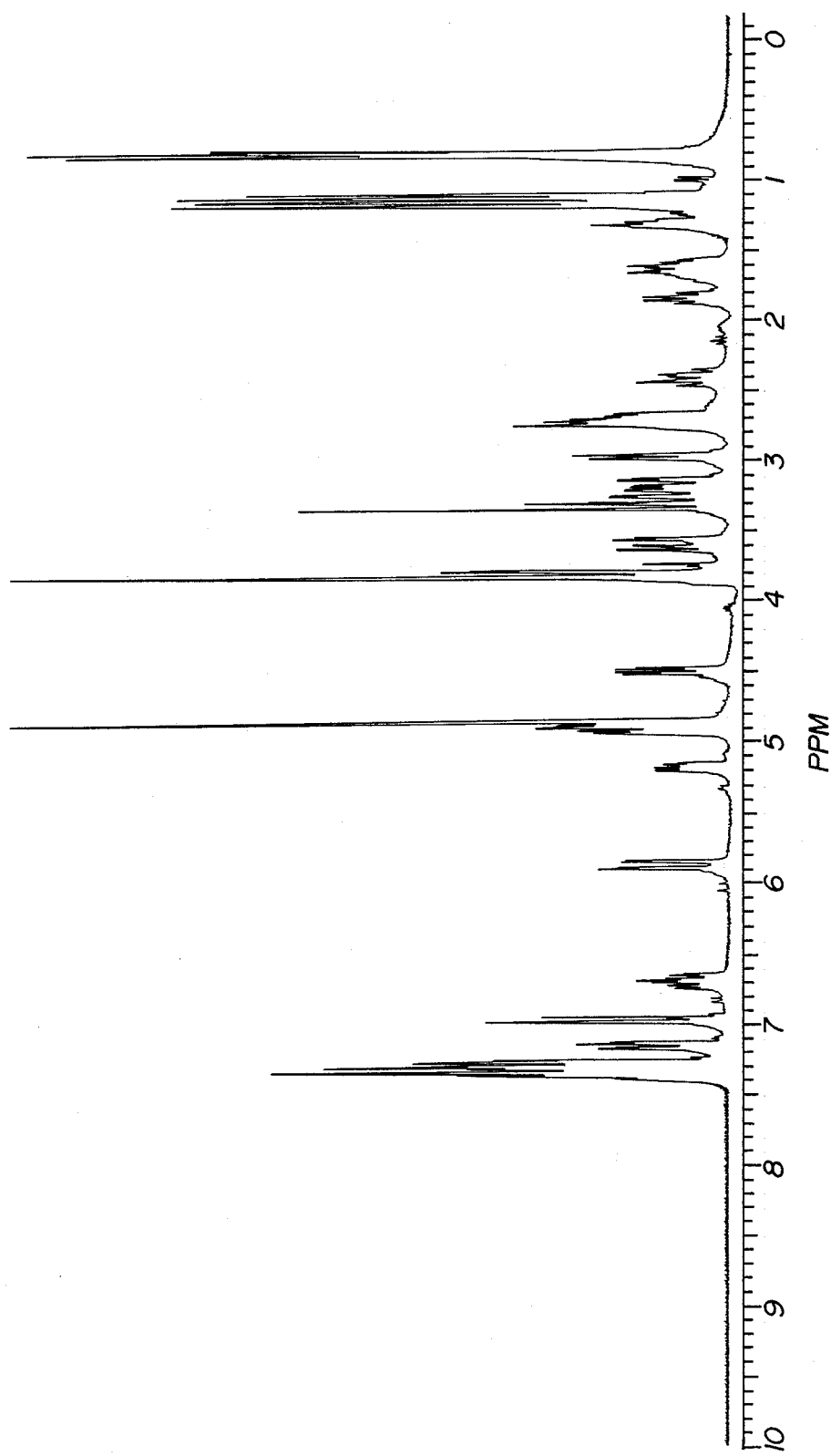

ANTIFUNGAL AGENT AND METHOD

DESCRIPTION OF THE INVENTION

The present invention is directed to new antifungal agents which may be repesented by the formula

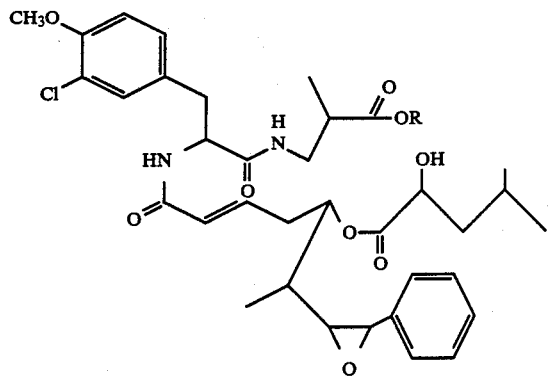

(I)

wherein R is H or lower alkyl.

When R is H, the compound may be identified also by the Chemical Abstracts nonmenclature of 5-[[2-[(2-carboxypropyl)-amino]-1-[(3-chloro-4-methoxyphenyl)methyl]-2-oxo-ethyl]amino]-5-oxo-1-[1-(3-phenyloxiranyl-)ethyl]-3-pentenyl 2-hydroxy-4-methylpentanoate. When R is alkyl it may be identified by a name in which a specific alkyl radical is substituted in the following nomenclature: 5-[[2-[[2-(alkoxycarbonyl)propyl]amino]-1-[(3-chloro-4-methoxyphenyl)methyl]-2-oxoethyl]amino-5-oxo-1-[1-(3-phenyloxiranyl)ethyl]-3-pentenyl 2-hydroxy-4-methylpentanoate. A preferred compound is one in which R is methyl and is therefore named 5-[[2-[[2-(methoxycarbonyl)propyl]amino]-1-[(3-chloro-4-methoxyphenyl)methyl]-2-oxoethyl]amino]-5-oxo-1-[1-(3-phenyloxiranyl)ethyl]-3-pentenyl 2-hydroxy-4-methylpentanoate. For convenience, the latter compound hereinafter shall be referred to as Compound Ia.

The compounds of the present invention identified by formula I are white or light colored solids, soluble in organic solvents and adaptable to be employed in solution. It is also adaptable to be employed in aqueous dispersions.

The compounds of the present invention may be produced from an antibiotic compound identifiable by the Chemical Abstracts nomenclature of 10-[(3-chloro-4-methoxyphenyl)methyl]-6-methyl-3-(2-methyl-propyl)-16-[1-(3-phenyloxiranyl)ethyl]-1,4-dioxa-8,11-diazacyclohexadec-13-ene-2,5,9,12-tetrone (Compound A) having the structure

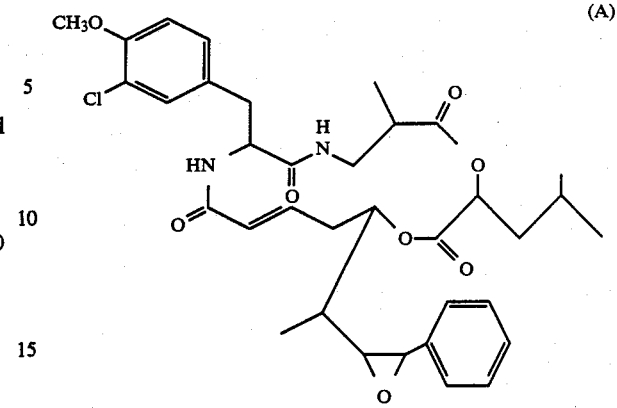

(A)

and disclosed and claimed in concurrently filed copending application Ser. No. 219,942 filed July 15, 1988 in the name of Hirsch et. al., and produced by cultivating an unidentified strain of Nostoc sp., ATCC 53789.

The compound of the present invention where R is $CH_3$ was initially discovered as the deutero analog after Compound A was allowed to stand in perdeuteromethanol at ambient temperature.

The compounds of the present invention (formula I) may be prepared by subjecting Compound A to conditions of hydrolysis or alcoholysis by placing it in a polar solvent, preferably under mild basic conditions (Lewis base) and stirring for time sufficient for reaction to occur with the formation of Compound I in the reaction mixture. Upon completion of the reaction, the contents of the flask may be evaporated to dryness to recover the desired product. If desired, further purification may be effected employing conventional procedures.

Reagents for carrying out the hydrolysis include 30 percent aqueous methanol solution, 1 percent potassium hydroxide in methanol, 0.1 M sodium hydroxide, aqueous ethanol or aqueous isopropanol and other mildly basic reagents. When the base is an alkali, the hydrolysis medium may be acidified with dilute acid such as 0.1N HCl or acetic acid. Reagents for ester formation by alcoholysis are the alcohols corresponding to the desired esters such as methanol, ethanol, isopropanol and the like. For ester formation, the alcohols should be substantially anhydrous.

The reaction is carried out at ambient temperature and the progress of the reaction may be monitored using a reverse phase high performance liquid chromatographic column (such as Zorbax ODS of siliceous microparticulate porous particles from DuPont; 21.2 mm×25 cm) and using 75/25 methanol/water as eluting agent. The retention time of Compound I is significantly different from that of Compound A.

The products are useful against fungi and thus are adapted to be employed in compositions for the control of fungi.

The angifungal properties are most effectively utilized when Compound I is formulated into antifungal treating compositions with a biologically inert carrier which in cases of use in pharmaceutical applications should also be pharmaceutically acceptable.

The novel compositions are formulated according to conventional compounding techniques with a biologically inert carrier, generally with the aid of a surface active dispersing agent. The compositions may contain 5 percent or more by weight of the active compound and, if a concentration composition, may contain 15 percent or more. In preparing the compositions, Compound I is intimately admixed with an appropriate carrier.

Suitable carriers include liquids such as water, glycol, oil, alcohols and the like which may include buffering agents, sodium chloride, dextrose and various suspending, stabilizing, solubilizing or dispersing agents. Solid carriers include starches, sugars, kaolin, ethyl cellulose, calcium carbonate, sodium carbonate, calcium phosphate, talc, lactose, lubricants such as calcium or magnesium stearate, binders, disintegrating agents and the like.

Compound I may also be formulated in creams and ointments such as white petrolatum, anhydrous lanolin, cetyl alcohol, cold cream, glyceryl monostearate, rose water and the like.

The antifungal compositions may be employed by applying to the area where fungal control is desired in such amounts as necessary to effect the desired control.

The following examples illustrate the invention but are not to be construed as limiting:

EXAMPLE I

Isolation of Compound Ia'

46 milligrams of purified Compound A obtained by the fermentation of Nostoc sp. in the manner hereinafter described and which had been standing in a concentrated solution of perdeuteromethanol for several hours was subsequently chromatographed on a reverse phase column (Zorbax ODS 21.2 mm.×25 cm) using 60/40 acetonitrile/water as eluant at a flow rate of 20 milliliters per minute. Twenty milliliter fractions were collected and monitored by analytical reverse phase HPLC and the fractions with like retention times combined. Combined fractions of $R_t=8.2$ and of $R_t=9.9$ were subjected to reduced pressure to remove volatiles and to obtain 13 milligrams of a Compound I in which R is perdeuteromethyl (hereinafter Compound Ia') and to recover 16 milligrams of Compound A.

The following spectral data were obtained for Compound Ia':

Mass Spectral Data

The molecular formula of Compound Ia' is $C_{36}H_{44}ClD_3N_2O_9$ (calc 689.3158; found 689.3189) by high resolution mass spectrometry (HRMS, electron impact). Characteristic fragment ions are observed at m/z 654 (M-CD$_3$OH), 438, 410, 412, 314, 195, and 155.

NMR Spectral Data $^{13}$C NMR chemical shifts obtained in CD$_3$OD at 75 MHz:
176.67, 175.78, 173.36, 167.55, 155.41, 140.67, 138.53, 121.88, 131.47, 129.81, 129.68(2C), 129.39, 127.35, 126.93(2C), 123.23, 113.47, 76.22, 70.42, 64.83, 60.16, 56.57, 56.19, 44.29, 42.98, 41.01, 40.54, 38.06, 35.64, 25.44, 23.65, 21.67, 15.04, 13.58.

$^1$H NMR spectrum in CD$_3$OD at 300 MHz is as seen in the accompanying drawing.

The $^1$H NMR and mass spectrum of Compound Ia' were in conformance with hydrolysis at the ester bond linking the beta amino butyric system with alpha hydroxy isovaleric system.

Compound Ia' has been found to be useful against pathogenic fungi such as *Cryptococcus neoformans*. Such activity may be illustrated with test results against *Cryptococcus neoformans* employing yeast nitrogen base dextrose agar medium. In carrying out the assay, Compound Ia' was solubilized in 10 percent dimethyl sulfoxide (DMSO) supplemented with one drop of Tween 20. Twofold dilutions were made with sterile distilled water/10 percent DMSO to obtain final drug concentrations in the agar dilution assay plates ranging from 0.008 to 16.0 μg/ml against an expanded panel of 84 *Cryptococcus neoformans* strains.

The minimum inhibitory concentration against the expanded panel of 84 *Cryptococcus neoformans* isolates may be summarized as follows:

| | Activity (μg/ml) |
| --- | --- |
| | Compound Ia' |
| G-MIC[a] | >6.11 |
| Range | 4.0->16.0 |
| MIC$_{50}$[b] | 8.0 |
| MIC$_{90}$[c] | 8.0 |

[a]geometric means of MIC
[b]concentration at which 50% of the strains were inhibited
[c]concentration at which 90% of the strains were inhibited

EXAMPLE II 10 milliliters of 30 percent aqueous methanol is added with stirring to 10 milligrams of Compound A at room temperature and the stirring continued after completion of the addition. The reaction mixture is monitored by sampling from time to time to assay for the disapperance of the retention time for Compound A by analytical reverse phase HPLC (Zorbax ODS 21.2 mm×25 cm, 75/25 methanol/water). On completion of the reaction as determined by the assay results, the eluate is evaporated to dryness to obtain Compound I where R is H.

EXAMPLE III 10 milliliters of anhydrous methanol is added with stirring to 10 milligrams of Compound A at room temperature and the stirring continued after completion of the addition. The reaction mixture is monitored by sampling to assay for the disappearance of the retention time for Compound A by analytical reverse phase HPLC using 75/25 methanol/water as eluting agent. On completion of the reaction as determined by the assay results, the eluate is evaporated to dryness to obtain Compound Ia (R is methyl).

EXAMPLE IV

In a similar manner, compounds of formula I may be prepared as follows:
(a) Compound of formula I in which R is H, by the reaction of Compound A and 0.1 M sodium hydroxide, followed by acidification.
(b) Compound of formula I in which R is CH$_3$CH$_2$, by the reaction of Compound A and anhydrous ethanol.
(c) Compound of formula I in which R is (CH$_3$)$_2$CH by the reaction of Compound A and anhydrous isopropyl alcohol.

Starting Material

The starting material for the synthesis of Compound I is a natural product identifiable by formula A and which may be obtained by the cultivation of a cyanobacteria (Nostoc sp.) ATCC 53789 and isolating it from either a methanol extract of the cells or from the filtered (or supernatant) broth.

The cultivation may be carried out by inoculating a tube of Nostoc sp. culture ATCC 53789 in BG-13 medium and the inoculated culture incubated at 25° C. under a continuously replenished atmosphere of 5 percent (v/v) carbon dioxide in air and under continuous illumination at 5000 lux. At the end of this period, the cells are transferred to a larger (2–10 fold) volume of medium and the medium similarly cultivated under an atmosphere of 5 percent carbon dioxide in air and under continuous illumination at 5000 lux for from 12–20 days to obtain the compound of formula A. The latter may be extracted from the cells with methanol. Some of the desired compound also may be found in the fermentation broth and extracted with ethyl acetate. Compound A may be recovered from the methanol extract by partitioning with methylene chloride and vaporizing the volatiles or from the ethyl acetate extract of the broth by vaporizing the volatiles and thereafter chromatographing the residue to purify the residue employing 75/25 methanol/water as eluant.

The production of Compound A from Nostoc sp is more fully described in the aforementioned copending application Ser. No. 219,942 filed July 15, 1988 of Hirsch et.al.

What is claimed is:

1. A compound represented by the formula

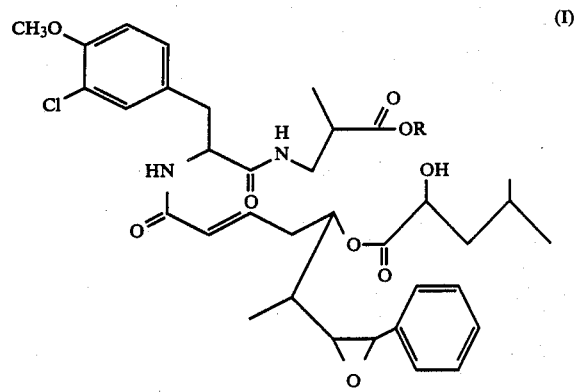

(I)

wherein R is H or lower alkyl.

2. 5-[[2-[[2-(Methoxycarbonyl)propyl)amino]-1-[(3-chloro-4-methoxyphenyl)methyl]-2-oxoethyl]amino]-5-oxo-1-[1-(3-phenyloxiranyl)ethyl]-3-pentenyl 2-hydroxy-4-methylpentanoate.

3. 5-[[2-[(2-Carboxypropyl)amino]-1-[(3-chloro-4-methoxyphenyl)methyl]-2-oxoethyl]amino]-5-oxo-1-[1-(3-phenyloxiranyl)ethyl]-3-pentenyl 2-hydroxy-4-methylpentanoate.

4. An antifungal composition which comprises a compound of claim 1 in admixture with a pharmaceutically acceptable carrier.

5. A method for controlling mycotic infections which comprises administering to an animal infected with fungi, an antifungally effective amount of the compound of claim 1.

* * * * *